(12) United States Patent
Trieu

(10) Patent No.: US 8,642,059 B2
(45) Date of Patent: *Feb. 4, 2014

(54) CONTROLLED RELEASE SYSTEMS AND METHODS FOR INTERVERTEBRAL DISCS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2169 days.

This patent is subject to a terminal disclaimer.

(21) Appl. No.: 11/410,216

(22) Filed: Apr. 24, 2006

(65) Prior Publication Data

US 2007/0250044 A1    Oct. 25, 2007

(51) Int. Cl.
  *A61B 17/56*    (2006.01)
  *A61F 17/00*    (2006.01)
  *A61K 9/22*     (2006.01)
  *A61F 2/44*     (2006.01)

(52) U.S. Cl.
  USPC ..... 424/422; 424/423; 604/890.1; 604/891.1; 604/892.1; 623/17.12

(58) Field of Classification Search
  USPC ......... 424/422, 423; 604/890.1, 891.1, 892.1; 623/17.12
  See application file for complete search history.

(56) References Cited

U.S. PATENT DOCUMENTS

| | | | |
|---|---|---|---|
| 3,320,131 A | 5/1967 | Smith | |
| 3,941,127 A | 3/1976 | Froning | |
| 3,964,480 A | 6/1976 | Froning | |
| 4,039,682 A | 8/1977 | Ausman et al. | |
| 4,374,926 A | 2/1983 | Stern | |
| 4,430,760 A | 2/1984 | Smestad | |
| 4,439,423 A | 3/1984 | Smith | |
| 4,696,816 A | 9/1987 | Brown | |
| 4,719,108 A | 1/1988 | Smith | |
| 4,904,260 A | 2/1990 | Ray et al. | |
| 5,422,103 A | 6/1995 | Stern et al. | |
| 5,456,679 A | 10/1995 | Balaban et al. | |
| 5,468,480 A | 11/1995 | Barrett et al. | |
| 5,645,549 A | 7/1997 | Boyd et al. | |
| 5,919,235 A | 7/1999 | Husson et al. | |
| 6,007,810 A | 12/1999 | Ishikawa et al. | |
| 6,063,378 A | 5/2000 | Nohara et al. | |
| 6,231,615 B1 | 5/2001 | Preissman | |
| 6,280,475 B1 | 8/2001 | Bao et al. | |
| 6,294,187 B1 | 9/2001 | Boyce et al. | |
| 6,471,688 B1 | 10/2002 | Harper et al. | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |
| 6,551,838 B2 | 4/2003 | Santini, Jr. et al. | |
| 6,656,162 B2 | 12/2003 | Santini, Jr. et al. | |
| 6,669,683 B2 | 12/2003 | Santini, Jr. et al. | |
| 6,773,429 B2 | 8/2004 | Sheppard, Jr. et al. | |
| 6,827,250 B2 | 12/2004 | Uhland et al. | |
| 6,849,463 B2 | 2/2005 | Santini, Jr. et al. | |
| 6,973,718 B2 | 12/2005 | Sheppard, Jr. et al. | |
| 6,976,982 B2 | 12/2005 | Santini, Jr. et al. | |
| 7,014,636 B2 | 3/2006 | Gilbert | |
| 7,163,545 B2 | 1/2007 | Yazemski et al. | |
| 7,217,293 B2 | 5/2007 | Branch, Jr. | |
| 2001/0020188 A1 | 9/2001 | Sander | |
| 2002/0026244 A1 | 2/2002 | Trieu | |
| 2002/0029083 A1 | 3/2002 | Zucherman et al. | |
| 2002/0087113 A1 | 7/2002 | Hartlaub | |
| 2002/0128202 A1 | 9/2002 | Carney et al. | |
| 2002/0173851 A1 | 11/2002 | McKay | |
| 2003/0009235 A1 | 1/2003 | Manrique et al. | |
| 2003/0039676 A1 | 2/2003 | Boyce et al. | |
| 2004/0031666 A1 | 2/2004 | Ostman | |
| 2004/0091540 A1 | 5/2004 | Desrosiers et al. | |
| 2004/0121486 A1 | 6/2004 | Uhland et al. | |
| 2004/0133280 A1 | 7/2004 | Trieu | |
| 2004/0143242 A1 | 7/2004 | Ludin et al. | |
| 2004/0176750 A1* | 9/2004 | Nelson et al. | 604/891.1 |
| 2004/0220552 A1 | 11/2004 | Heruth et al. | |
| 2005/0031666 A1* | 2/2005 | Trieu | 424/426 |
| 2005/0070778 A1 | 3/2005 | Lackey et al. | |
| 2005/0071009 A1 | 3/2005 | Muhanna et al. | |
| 2006/0004456 A1 | 1/2006 | McKay | |
| 2006/0046961 A1 | 3/2006 | Mckay et al. | |
| 2006/0047341 A1 | 3/2006 | Trieu | |

(Continued)

FOREIGN PATENT DOCUMENTS

WO    WO 96/34093    10/1996
WO    01045577 A3    6/2001

(Continued)

OTHER PUBLICATIONS

Chymopapain from GenBank Accession No. CAA66378, pp. 1-2. Accessed May 14, 2009.
Collagenase from GenBank Accession No. CAA07432, pp. 1-3. Accessed May 14, 2009.
Fibroblast growth factor from GenBank Accession No. CAA41788, pp. 1-2. Accessed May 14, 2009.
Morphogenetic protein from GenBank Accession No. NP_391488, pp. 1-3. Accessed May 14, 2009.
Albumin from GenBank Accession No. CAA00606, pp. 1-2. Accessed May 14, 2009.
Sheikh H et al. 2009. In vivo intervertebral disc regeneration using stem cell-derived chondroprogenitors. J Neurosurg Spine 10: 265-272.

(Continued)

*Primary Examiner* — Blessing M Fubara
*Assistant Examiner* — Kauser M Akhoon
(74) *Attorney, Agent, or Firm* — Sorell, Lenna and Schmidt LLP

(57) ABSTRACT

A device includes a sensor configured to determine a condition associated with a nucleus pulposus, a reservoir configured to include a first agent capable of affecting the condition associated with the nucleus pulposus, a control element configured to provide access to the reservoir, and a controller in communication with the sensor and the control element. The controller is configured to manipulate the control element to provide access to the reservoir in response to the condition determined by the sensor.

21 Claims, 12 Drawing Sheets

(56) References Cited

U.S. PATENT DOCUMENTS

| | | |
|---|---|---|
| 2006/0271112 A1* | 11/2006 | Martinson et al. ............ 607/2 |
| 2007/0003598 A1 | 1/2007 | Trieu |
| 2007/0122446 A1 | 5/2007 | Trieu |
| 2007/0128575 A1 | 6/2007 | Trieu |
| 2007/0250044 A1 | 10/2007 | Trieu |
| 2007/0250045 A1 | 10/2007 | Trieu |
| 2007/0250046 A1 | 10/2007 | Trieu |
| 2007/0276337 A1 | 11/2007 | Trieu |

FOREIGN PATENT DOCUMENTS

| | | |
|---|---|---|
| WO | 0217824 A3 | 3/2002 |
| WO | 03068149 A3 | 8/2003 |
| WO | 2004047691 A | 6/2004 |
| WO | WO 2004/101015 A2 | 11/2004 |
| WO | 2005014071 A1 | 2/2005 |
| WO | 2005065079 A2 | 7/2005 |
| WO | 2005092249 A1 | 10/2005 |
| WO | WO 2005/102440 A2 | 11/2005 |
| WO | WO 2005/115438 A1 | 12/2005 |
| WO | WO 2006/017456 A2 | 2/2006 |
| WO | 2006050106 A | 5/2006 |
| WO | 2006055547 A | 5/2006 |
| WO | 2007127548 A | 11/2007 |
| WO | 2008030832 A1 | 3/2008 |
| WO | 2008030963 A1 | 3/2008 |

OTHER PUBLICATIONS

Bron JL et al. 2009. Repair, regenerative and supportive therapies of the annulus fibrosus: achievements and challenges. Eur Spine J 18:301-313.

* cited by examiner

1

CONTROLLED RELEASE SYSTEMS AND METHODS FOR INTERVERTEBRAL DISCS

FIELD OF THE DISCLOSURE

The present disclosure relates generally to controlled release devices. More specifically, the present disclosure relates to controlled release devices for implanting in an intervertebral disc.

BACKGROUND

In human anatomy, the spine is a generally flexible column that can take tensile and compressive loads. The spine also allows bending motion and provides a place of attachment for keels, muscles and ligaments. Generally, the spine is divided into four sections: the cervical spine, the thoracic or dorsal spine, the lumbar spine, and the pelvic spine. The pelvic spine generally includes the sacrum and the coccyx. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column can be subjected. At the same time, the intervertebral discs can allow adjacent vertebral bodies to move relative to each other, particularly during bending or flexure of the spine. Thus, the intervertebral discs are under constant muscular and gravitational pressure and generally, the intervertebral discs are the first parts of the lumbar spine to show signs of deterioration.

In particular, deterioration can be manifested as a herniated disc. Weakness in an annulus fibrosis can result in a bulging of the nucleus pulposus or a herniation of the nucleus pulposus through the annulus fibrosis. Ultimately, weakness of the annulus fibrosis can result in a tear permitting the nucleus pulposus to leak from the intervertebral space. Loss of the nucleus pulposus or a bulging of the nucleus pulposus can lead to pinching of nerves and contact between osteal surfaces, causing pain and damage to vertebrae. In addition, aging can lead to a reduction in the hydration of the nucleus pulposus. Such a loss in hydration can also permit contact between osteal surfaces and pinching of nerves.

While replacement of the disc in the intervertebral space with an implant is an option, many surgeons seek a less invasive procedure. One such procedure for alleviating a bulging disc is injection of chemonucleolytic agents to dissolve a portion of the nucleus pulposus, drawing the herniated or bulging portion of the nucleus pulposus back to the center of the intervertebral disc. However, such injections can leak into sensitive regions outside of the intervertebral disc, leading to medical complications. Other attempts to alleviate bulging discs include implanting slowly dissolving solid matrices that include a chemonucleolytic agent. Once implanted, the solid matrices slowly dissolve, substantially releasing the chemonucleolytic agent, sometimes resulting in degradation of an excess amount of the nucleus pulposus.

DESCRIPTION OF DRAWINGS

Figure 1:
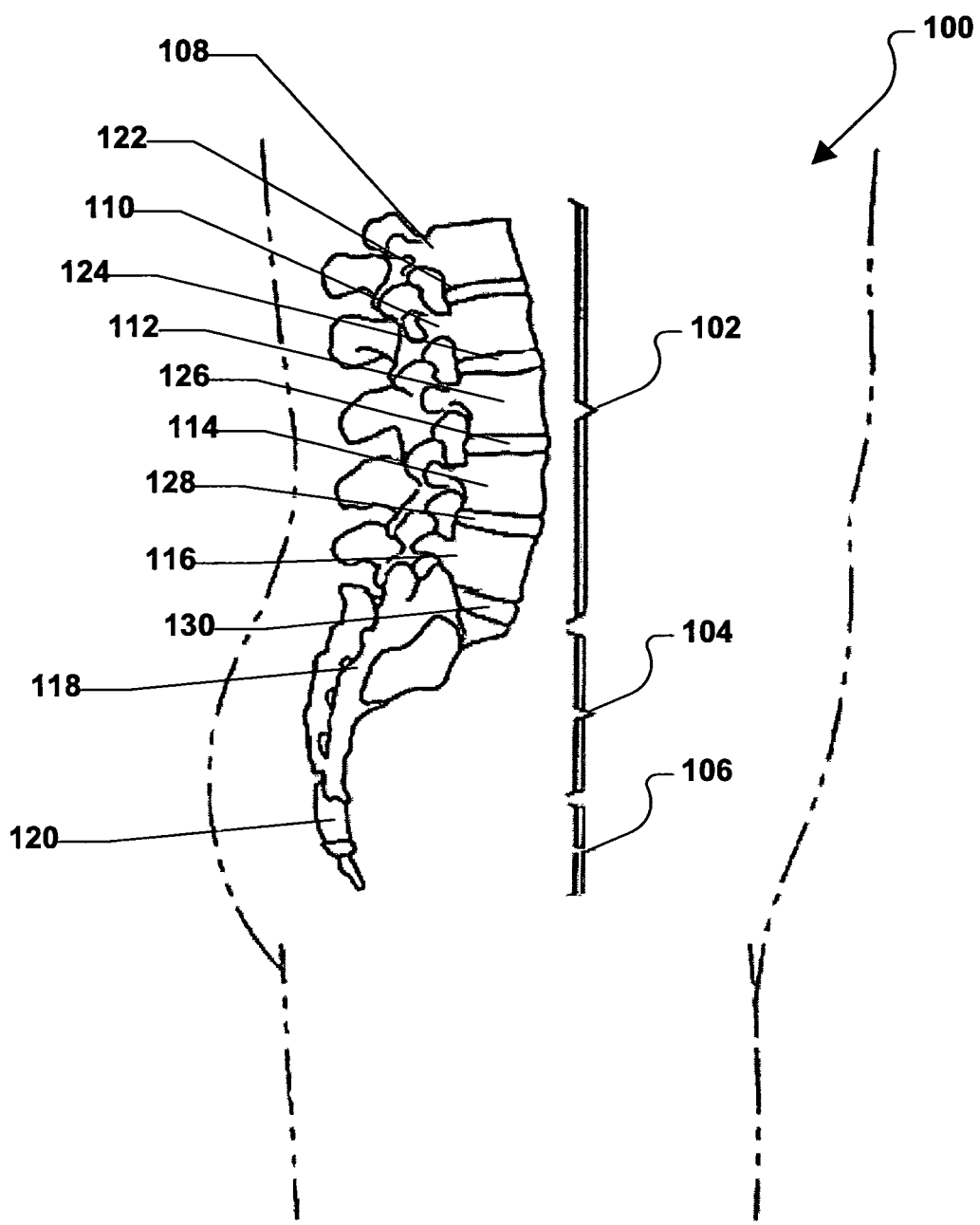
FIG. 1 includes a lateral view of a portion of a vertebral column.

In a particular embodiment, a controlled release device includes a sensor, a controller, and at least one reservoir to store an agent. The agent can influence a condition of a nucleus pulposus. For example, the agent can be a stimulating agent to increase hydration of the nucleus pulposus. In another example, the agent can be a degrading agent, such as a nucleolytic agent. The controlled release device is configured to selectively release the agent in response to a signal received from the sensor. In a particular example, the controller receives a signal from the sensor indicative of a condition of the nucleus pulposus and selectively releases the agent to affect the condition.

In a particular embodiment, a device includes a sensor configured to determine a condition associated with a nucleus pulposus, a reservoir configured to include a first agent capable of affecting the condition associated with the nucleus pulposus, a control element configured to provide access to the reservoir, and a controller in communication with the sensor and the control element. The controller is configured to manipulate the control element to provide access to the reservoir in response to the condition determined by the sensor.

In another exemplary embodiment, a device includes a sensor configured to determine a condition associated with a nucleus pulposus, a first reservoir configured to include a stimulating agent, a second reservoir configured to include a degrading agent, and a controller in communication with the sensor. The controller is configured to selectively initiate access to the first reservoir or the second reservoir in response to the condition determined by the sensor.

In a further exemplary embodiment, a device includes a pressure transducer, a first reservoir including a stimulating agent, a second reservoir including a degrading agent, a first control element configured to provide access to the first reservoir, a second control element configured to provide access to the second reservoir, a reservoir driver configured to motivate at least one of the stimulating agent from the first reservoir or the degrading agent from the second reservoir, and a controller in communication with the pressure transducer, the first control element, and the second control element. The controller is configured to manipulate the first and second control elements based on a signal received from the pressure transducer.

In an additional embodiment, a method of treating a spinal disc includes determining a condition associated with a nucleus pulposus using a sensor located at least partially in the nucleus pulposus and includes selectively releasing an agent to affect the condition associated with the nucleus pulposus from a reservoir based on the condition associated with the nucleus pulposus.

In another exemplary embodiment, a device includes a first reservoir including a first agent, a first reservoir driver coupled to the reservoir and configured to effect the release of the agent from the reservoir, and a remote access component. The device is configured to manipulate the reservoir driver to effect the release of the agent in response to a first signal received via the remote access component.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged that intervertebral lumbar disc 122, 124, 126, 128, 130 can be at least partially treated with an intervertebral implanted device according to one or more of the embodiments described herein. In a particular embodiment, a controlled release device can be inserted into the intervertebral lumbar disc 122, 124, 126, 128, 130.

Figure 2:
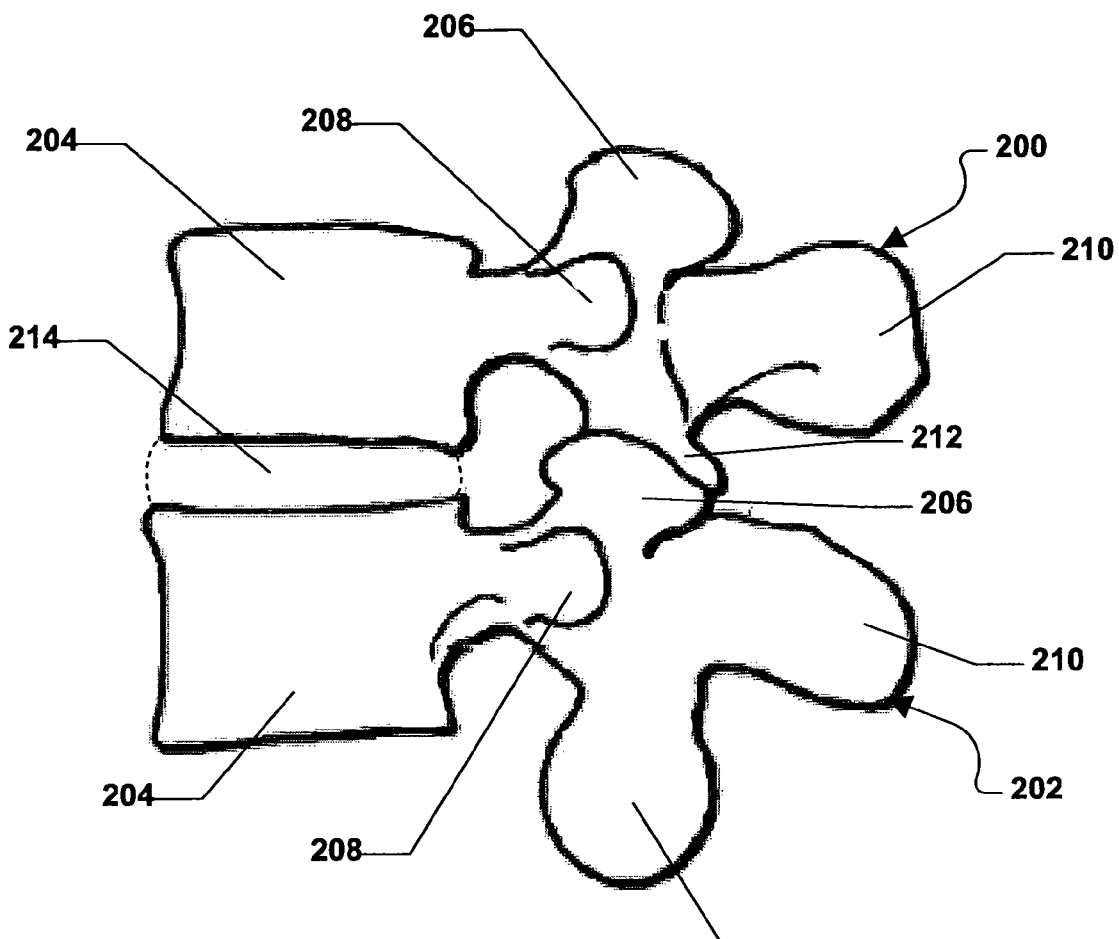
FIG. 2 includes a lateral view of a pair of adjacent vertebrae.

FIG. 2 depicts a detailed lateral view of two adjacent vertebrae, e.g., two of the lumbar vertebra 108, 110, 112, 114, 116 illustrated in FIG. 1. FIG. 2 illustrates a superior vertebra 200 and an inferior vertebra 202. As illustrated, each vertebra 200, 202 includes a vertebral body 204, a superior articular process 206, a transverse process 208, a spinous process 210 and an inferior articular process 212. FIG. 2 further depicts an intervertebral disc 214 between the superior vertebra 200 and the inferior vertebra 202. As described in greater detail below, an intervertebral controlled release device according to one or more of the embodiments described herein can be installed within the intervertebral disc 214 between the superior vertebra 200 and the inferior vertebra 202.

Figure 3:
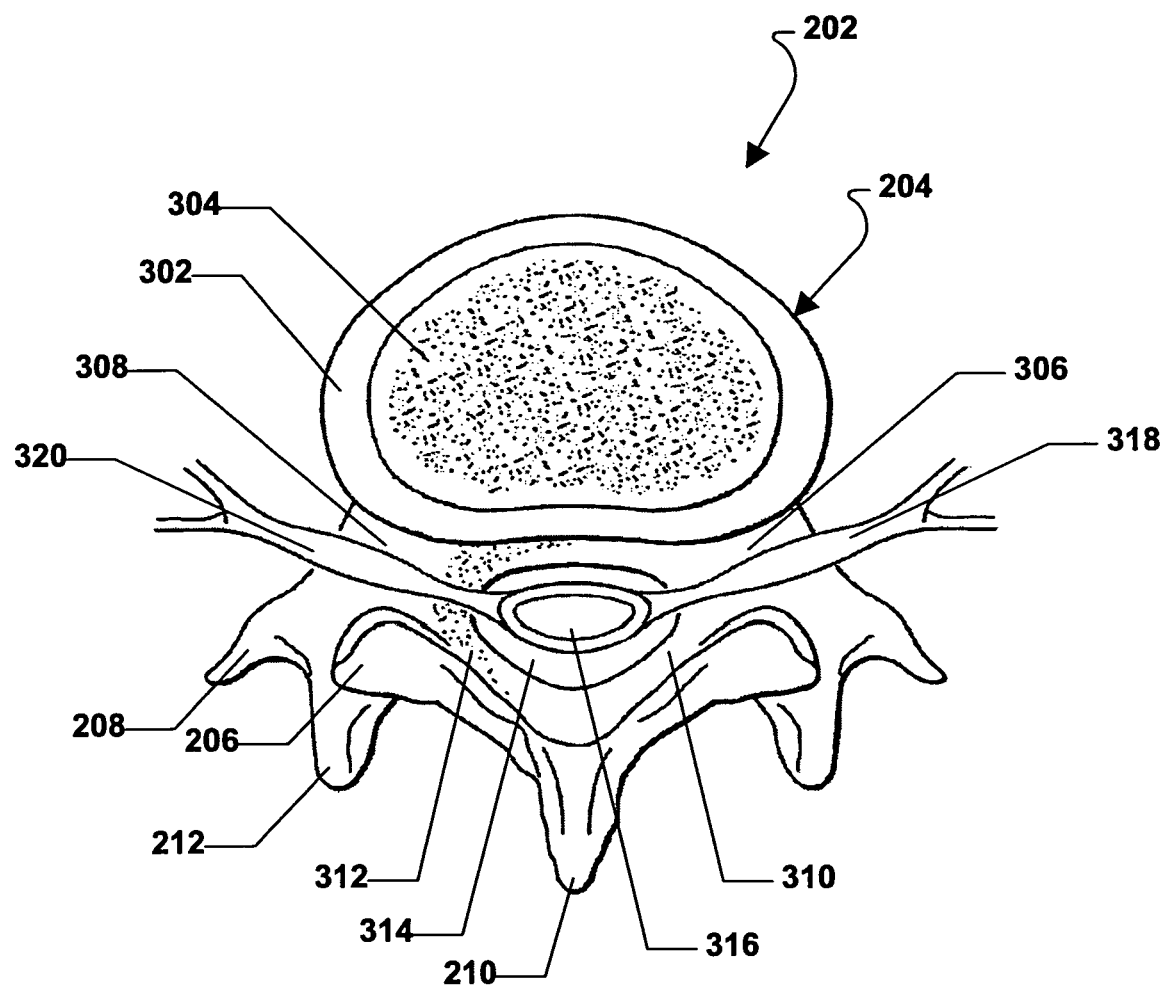
FIG. 3 includes a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
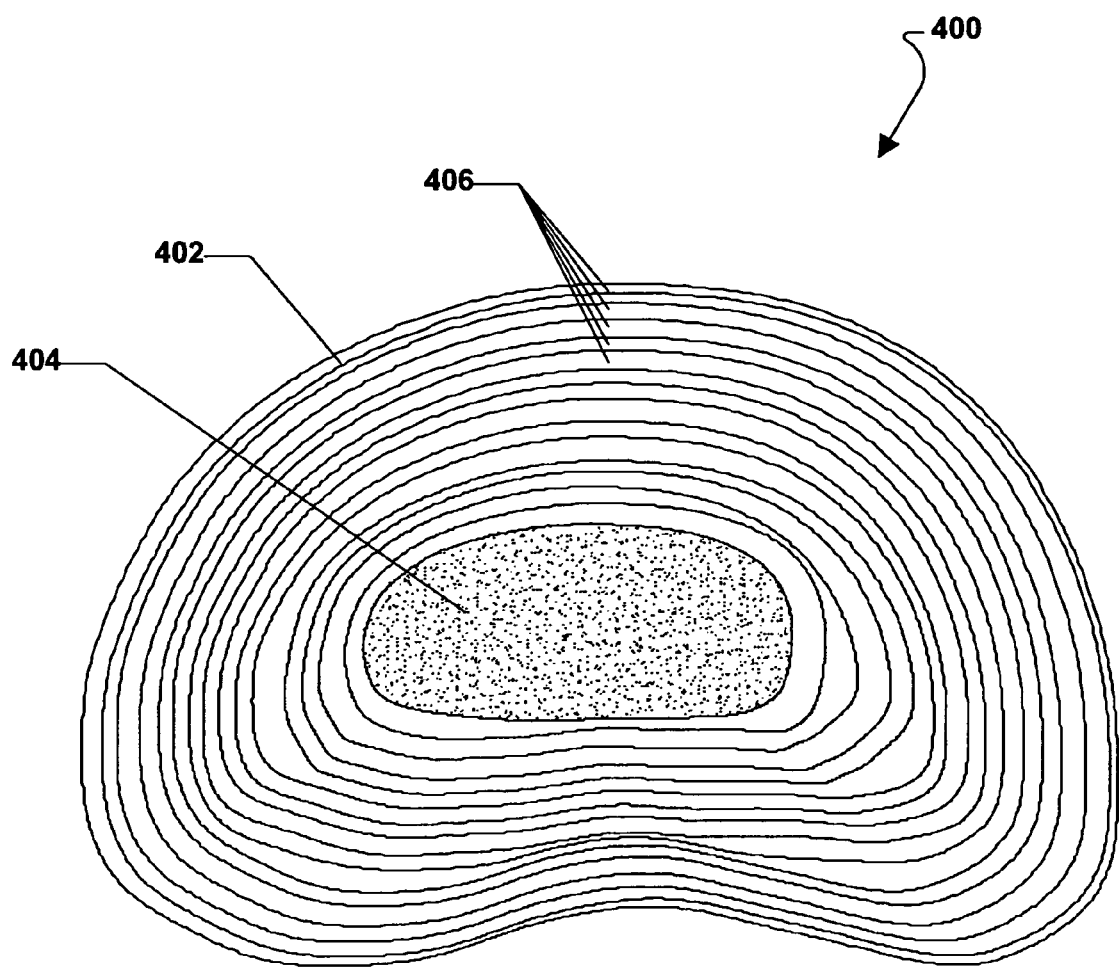
FIG. 4 includes a cross section view of an intervertebral disc.

Referring now to FIG. 4, an intervertebral disc is shown and is generally designated 400. The intervertebral disc 400 is made up of two components: the annulus fibrosis 402 and the nucleus pulposus 404. The annulus fibrosis 402 is the outer portion of the intervertebral disc 400, and the annulus fibrosis 402 includes a plurality of lamellae 406. The lamellae 406 are layers of collagen and proteins. Each lamella 406 includes fibers that slant at 30-degree angles, and the fibers of each lamella 406 run in a direction opposite the adjacent layers. Accordingly, the annulus fibrosis 402 is a structure that is exceptionally strong, yet extremely flexible.

The nucleus pulposus 404 is the inner gel material that is surrounded by the annulus fibrosis 402. It makes up about forty percent (40%) of the intervertebral disc 400 by weight. Moreover, the nucleus pulposus 404 can be considered a ball-like gel that is contained within the lamellae 406. The nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of the annulus fibrosis 402 can allow the nucleus pulposus 404 to be squeezed through the annulus fibers either partially, causing the disc to bulge, or completely, allowing the disc material to escape the intervertebral disc 400. The bulging disc or nucleus material can compress the nerves or spinal cord, causing pain. Accordingly, the nucleus pulposus 404 can be treated with an implantable controlled release device to improve the condition of the intervertebral disc 400.

Description of Agents

In an exemplary embodiment, a device to be implanted at least partially in the nucleus pulposus of an intervertebral disc includes at least one reservoir to store an agent. The agent can generally affect a condition of the nucleus pulposus. For example, the agent can decrease the hydration level of the nucleus pulposus or can cause a degeneration of the nucleus pulposus that leads to a reduction in hydration level, to a reduction in pressure, or to a reduction in size of the nucleus pulposus within the intervertebral disc. An agent causing a degeneration of the disc or reduction in hydration level is herein termed a "degrading agent." In another example, an agent can increase the hydration level of the nucleus pulposus or can cause a regeneration of the nucleus pulposus that results in an increase in hydration level or in an increase in pressure within the intervertebral disc. Such an agent that can cause an increase in hydration or that can cause a regeneration of the nucleus pulposus is herein termed a "regenerating agent." In a further example, an agent (herein termed a "therapeutic agent") can inhibit degradation of the nucleus pulposus or enhance maintenance of the nucleus pulposus. Herein, therapeutic agents and regenerating agents are collectively referred to as "stimulating agents."

An exemplary degrading agent can reduce hydration levels in the nucleus pulposus or can degrade the nucleus pulposus, resulting in a reduction in hydration level or in pressure within the intervertebral disc. For example, the degrading agent can be a nucleolytic agent that acts on portions of the nucleus pulposus. In an example, the nucleolytic agent is proteolytic, breaking down proteins.

An exemplary nucleolytic agent includes a chemonucleolysis agent, such as chymopapain, collagenase, chondroitinase, keratanase, human proteolytic enzymes, papaya protenase, or any combination thereof. An exemplary chondroitinase can include chondroitinase ABC, chondroitinase AC, chondroitinase ACII, chondroitinase ACE, chondroitinase B, chondroitinase C, or the like, or any combination thereof. In another example, a keratanase can include endo-β-galactosidase derived from *Escherichia freundii*, endo-β-galactosidase derived from *Pseudomonas* sp. IFO-13309 strain, endo-β-galactosidase produced by *Pseudomonas reptilivora*, endo-β-N-acetylglucosaminidase derived from *Bacillus sp.* KsT36, endo-β-N-acetylglucosaminidase derived from *Bacillus circulans* KsT202, or the like, or any combination thereof. In a particular example, the degrading agent includes chymopapain. In another example, the degrading agent includes chondroitinase-ABC.

An exemplary regenerating agent includes a growth factor. The growth factor can be generally suited to promote the formation of tissues, especially of the type(s) naturally occurring as components of an intervertebral disc. For example, the growth factor can promote the growth or viability of tissue or cell types occurring in the nucleus pulposus, such as nucleus pulposus cells or chondrocytes, as well as space filling cells, such as fibroblasts, or connective tissue cells, such as ligament or tendon cells. Alternatively or in addition, the growth factor can promote the growth or viability of tissue types occurring in the annulus fibrosis, as well as space filling cells, such as fibroblasts, or connective tissue cells, such as ligament or tendon cells. An exemplary growth factor can include transforming growth factor-β (TGF-β) or a member of the TGF-β superfamily, fibroblast growth factor (FGF) or a member of the FGF family, platelet derived growth factor (PDGF) or a member of the PDGF family, a member of the hedgehog family of proteins, interleukin, insulin-like growth factor (IGF) or a member of the IGF family, colony stimulating factor (CSF) or a member of the CSF family, growth differentiation factor (GDF), cartilage derived growth factor (CDGF), cartilage derived morphogenic proteins (CDMP), bone morphogenetic protein (BMP), or any combination thereof. In particular, an exemplary growth factor includes transforming growth factor P protein, bone morphogenetic protein, fibroblast growth factor, platelet-derived growth factor, insulin-like growth factor, or any combination thereof.

An exemplary therapeutic agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, an inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof. Another exemplary therapeutic agent can include Adalimumab, Infliximab, Etanercept, Pegsunercept (PEG sTNF-R1), Onercept, Kineret®, sTNF-R1, CDP-870, CDP-571, CNI-1493, RDP58, ISIS 104838, 1→3-β-D-glucan, Lenercept, PEG-sTNFRII Fc Mutein, D2E7, Afelimomab, AMG 108, 6-methoxy-2-napthylacetic acid or betamethasone, capsaiein, civanide, TNFRc, ISIS2302 and GI 129471, integrin antagonist, alpha-4 beta-7 integrin antagonist, cell adhesion inhibitor, interferon gamma antagonist, CTLA4-Ig agonist/antagonist (BMS-188667), CD40 ligand antagonist, Humanized anti-IL-6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-1 0, HuMax IL-15 (anti-IL 15 antibody), or any combination thereof.

In addition, pain medication can be incorporated within the reservoir in which the agent is contained or in a separate reservoir. An exemplary pain medication includes codeine, propoxyphene, hydrocodone, oxycodone, or any combination thereof.

Each of the agents can be maintained in liquid, gel, paste, slurry, or solid form, or any combination thereof. Solid forms include powder, granules, microspheres, miniature rods, or embedded in a matrix or binder material, or any combination thereof. In an example, fluids or water from surrounding tissues can be absorbed by device and placed in contact with drug in solid forms prior to release. Further, a stabilizer or a preservative can be included with the agent to prolong activity of the agent.

Description of a Device

Figure 5:
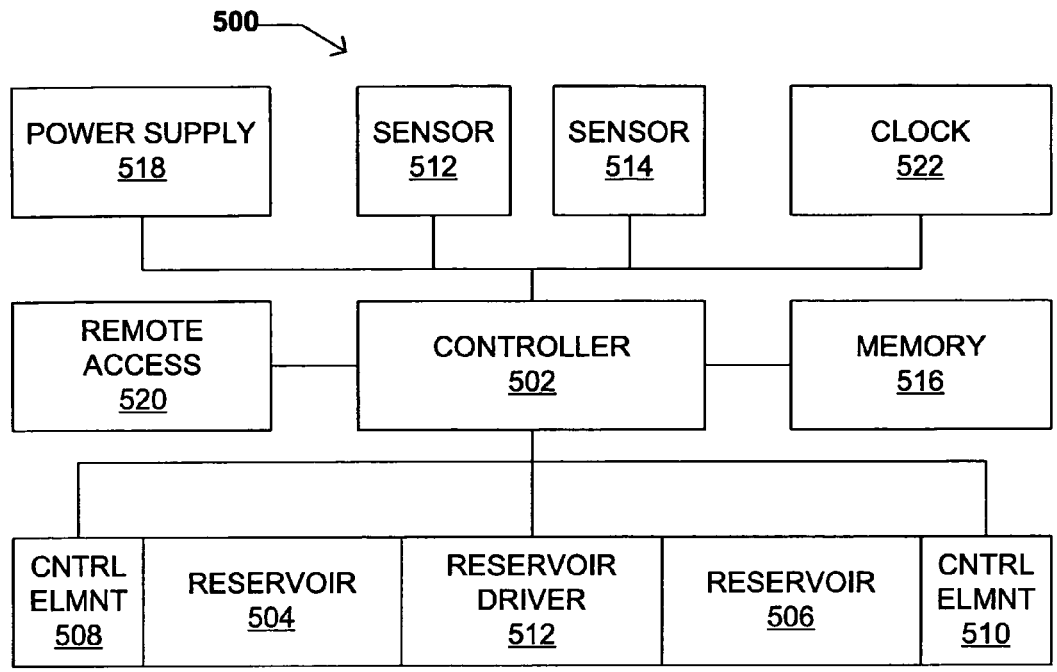
FIG. 5 includes a diagram of a controlled release device.

In a particular embodiment, an implantable device includes a sensor, a controller, and a reservoir to store an agent. FIG. 5 includes an illustration of an exemplary device 500. The exemplary device 500 includes a controller 502. A sensor, such as the sensors 512 and 514, can be in communication with the controller 502. In addition, the device 500 can include a reservoir, such as the reservoirs 504 and 506. The controller 502 can be communicatively coupled to a control element, such as the control elements 508 and 510, associated with the reservoir, such as the reservoirs 504 and 506, respectively. In addition, the controller 502 can be communicatively coupled to a reservoir driver 512 that can motivate movement of an agent from the reservoir, such as the reservoirs 504 and 506.

In an exemplary embodiment, the controller 502 can receive a signal from the sensor (512 or 514) and in response, manipulate the control element (508 or 510). For example, the controller 502 can include control circuitry, such as an algorithmic or arithmetic control circuitry. In an example, the controller 502 includes a proportional, integral, or differential (PID) controller. Alternatively, the controller 502 can include a processor configured to received sensor data, such as data from the sensors 512 or 514, and determine a dosage to be delivered. Based on the dosage, the processor can manipulate the control elements 508 or 510 or the reservoir driver 512. For example, the controller 502 can apply sensor data to an algorithm, an arithmetic model, an artificial intelligence engine, a threshold, or any combination thereof to determine a dosage or control protocol. An exemplary artificial intelligence engine includes a neural network, a fuzzy logic engine, a complex control model, or any combination thereof. In a further example, the controller 502 can perform calculations using the sensor data to determine, for example, a time average, a minimum value, a maximum value, a median value, a rate of change, a trend, or any combination thereof. Further, measurements can be selected or selectively weighted based on the time of day in which taken. For example, pressure data measured at a time at which a patient is typically asleep can be selected in contrast to pressure data measured during periods of high activity.

In an exemplary embodiment, the device 500 includes one or more sensors, such as sensors 512 or 514. An exemplary sensor (512 or 514) can include a pressure transducer, a moisture or hydration sensor, a pH sensor, a resistance or conductance meter, an electrolyte detector, or any combination thereof. Based on signals produced by the one or more sensors (512 or 514), the controller 502 can selectively initiate the release of an agent. In addition, the controller 502 can store sensor data in a memory 516.

The device 500 can also include one or more reservoirs, such as reservoirs 504 or 506. The reservoir (504 or 506) can include an agent, such as a stimulating agent or a degrading agent. In a particular example, the device 500 includes a reservoir 504 that includes a stimulating agent and includes a reservoir 506 that includes a degrading agent. The reservoirs (504 or 506) can be configured to store the agent in a liquid, gel, paste, slurry, or solid forms, or any combination thereof. A solid form can include powder, granule, microsphere, miniature rod, agent embedded in a matrix or binder material, or any combination thereof. In a solid form example, fluids or water from surrounding tissues can be absorbed by the device 500 and placed in contact with an agent in solid form prior to release. In a further example, the reservoir (504 or 506) can include a refill port.

A reservoir driver 512 can be coupled to the reservoir (504 or 506). As illustrated, the reservoir driver 512 can be coupled to both the reservoir 504 and the reservoir 506. Alternatively, a separate reservoir driver can be connected to each reservoir (504 or 506). An exemplary reservoir driver 512 can include a pump. For example, a pump can add fluid or water from surrounding tissue to a chamber that applies pressure to the reservoir (504 or 506), motivating an agent from the reservoir (504 or 506). In another example, the pump can add water or fluid directly to the reservoir (504 or 506) to increase pressure within the chamber or to hydrate a solid form agent within the reservoir (504 or 506).

In another example, the reservoir driver 512 can include an osmotic driver. For example, a membrane can separate a chamber from surrounding tissue. An osmotic agent within the chamber can absorb water or fluid from the surrounding tissue and expand or increase pressure within the chamber. The osmotic agent can include a non-volatile water-soluble osmagent, an osmopolymer that swells on contact with water, or a mixture of the two. An osmotic agent, such as sodium chloride with appropriate lubricants, binders, or viscosity modifying agents, such as sodium carboxymethylcellulose or sodium polyacrylate can be prepared in various forms. Sodium chloride in tablet form is a water swellable agent. The osmotic agent can generate between about 0 and about 36 MPa (about 5200 psi) of pressure. Materials suitable for the fluid permeable membrane include those that are semipermeable and that can conform to the shape of the housing upon wetting and make a watertight seal with the rigid surface of the housing. The polymeric materials from which the membrane can be made vary based on the pumping rates and device configuration requirements and can include plasticized cellulosic materials, enhanced polymethylmethacrylate such as hydroxyethylmethacrylate (HEMA), elastomeric materials such as polyurethanes and polyamides, polyether-polyamide copolymers, thermoplastic copolyesters, or the like, or any combination thereof. The chamber can apply pressure to a movable barrier between the chamber and the reservoir (504 or 506), motivating agent from the reservoir (504 or 506).

In a further example, the reservoir driver 512 can include a mechanical system that motivates agent from the reservoir (504 or 506). For example, the mechanical system can include a piston, a rotating screw, or any combination thereof.

In the exemplary device 500, a control element, such as the control elements 508 or 510, can be connected to the reservoir, such as the reservoirs 504 or 506, respectively. The control element (508 or 510) can permit access to the respective reservoir (504 or 506). For example, the control element (508 or 510) can include a valve that permits fluid agent to exit the reservoir (504 or 506). In another example, the control element (508 or 510) can include a pump that removes fluid agent from the reservoir (504 or 506). In a further example, the control element (508 or 510) can include a door that permits solid form agent to be pushed from the reservoir (504 or 506).

In an exemplary embodiment, the control element (508 or 510) and the reservoir driver 512 can be the same device. For example, a pump can both motivate the agent from the reservoir (504 or 506) and control the flow of the agent. In another example, a mechanical driver can act to both motivate and control the amount of agent exiting the reservoir (504 or 506).

In a further exemplary embodiment, the control element (508 or 510) can include a destructible or removable barrier. For example, individual reservoirs (504 or 506) can include a single dose of an agent. An array of reservoirs can be provided that each includes a removable barrier. Destruction or removal of the barrier exposes the contents of the reservoir to surrounding tissue. For example, the barrier can be a thin film that bursts when an agent within the reservoir is heated or activated. In another example, the barrier can be a film that when heated or exposed to electric current disintegrates, exposing a reservoir.

The device 500 can also include a memory 516 in communication with the controller 502. The controller 502 can store sensor data at the memory 516. In another example, the controller 502 can store parameter values that are accessed to determine control actions. For example, the controller 502 can store threshold values, model parameters, dosage parameters, or any combination thereof at the memory 516. As illustrated, the controller 502 is directly coupled to the memory 516. Alternatively, the controller 502 can communicate with a memory controller that in turn controls the memory 516. An exemplary memory 516 can include random access memory (RAM).

In addition, the device 500 can include a clock 522. The clock 522 can provide a time signal to the controller 502. The controller 502, for example, can use the time signal to time stamp sensor data. In another example, the controller 502 can use the time signal in performing calculations based on the sensor signal. For example, the controller 502 can select or weight sensor signals based on time of day. In another example, the controller can determine a minimum or maximum value of the sensor signal for a 24-hour period. In a further example, the controller 502 can determine a rate of change or a trend based on the time signal and sensor data.

The device 500 can further include a power supply 518. For example, the power supply 518 can include a battery. In an exemplary embodiment, the battery is a rechargeable battery. The power supply 518 can include a wireless power regeneration circuitry, such as an induction coil, or can include a recharging port. For example, the induction coil can respond to an electromagnetic signal and generate power for storage in a battery. In the example illustrated, the power supply 518 is coupled to the controller 502.

In an exemplary embodiment, the device 500 can include a remote access component 520. The remote access component 520 can be in communication with the controller 502. In an example, the remote access component 520 can respond to a magnetic field. In another example, the remote access component 520 can respond to an electromagnetic signal, such as a radio frequency signal. In a further example, the remote access component 520 can respond to a light signal, such as an infrared signal. In an additional example, the remote access component 520 can respond to a wave signal, such as an ultrasonic signal.

In response to a signal from the remote access component 520, the controller 502 can activate or change mode. In an example, the controller 502 can initiate control of the control element (508 or 510) or reading of the sensor (512 or 514) in response to a signal from the remote access component 520. In another example, the controller 502 can cease control or reading of components in response to a signal from the remote access component 520. In another exemplary embodiment, the controller 502 can communicate data via an antenna included within the remote access component 520. For example, sensor data stored in the memory 516 can be transmitted via the antenna.

In a further exemplary embodiment, the remote access component 520 can receive data for use by the controller 502. For example, the data can include control parameters, dosage parameters, timing parameters for data storage, time and date, programming instructions, or any combination thereof. An exemplary control parameter includes a threshold value, an algebraic constant, a model parameter, or any combination thereof.

In an alternative embodiment, the device can include a remote access component 520 that directly manipulates the control element (508 or 510) or the reservoir driver 512. For example, the remote access component 520 can directly manipulate the control element 508, such as a valve. In another example, the remote access component 520 can directly manipulate the reservoir driver 512. In a particular example, the device 500 includes a reservoir 504 including an agent, a reservoir driver 512 coupled to the reservoir and configured to effect the release of the agent from the reservoir 504, and a remote access component 520. In this particular example, the device 500 can be configured to manipulate the reservoir driver 512 to effect the release of the agent in response to a first signal received via the remote access component 520. For example, the control element 508 can be a valve that opens or closes in response to pressure in the reservoir 504. The reservoir driver 512 can increase the pressure in the reservoir 504 to open or close the valve. In addition, the device 500 can be configured to manipulate the reservoir driver 512 to prevent release of the agent in response to a second signal received via the remote access component 520.

In a further example, the device 500 can include a second reservoir 508 including a second agent. For example, the first agent can be a degrading agent and the second agent can be a stimulating agent. In a device including a single reservoir driver 508, the reservoir driver 512 can be coupled to the second reservoir 508. In another embodiment, the device 500 can include a second reservoir driver coupled to the second reservoir 508. The device 500 can be configured to manipulate the second reservoir driver to effect the release of the second agent. In a particular embodiment, the remote access component 520 can be configured to communicate using an IEEE 802.15 communication protocol.

In a particular example, a patient in which the device 500 is implanted can experience pain or a test of the patient, such as a computed tomography (CT) scan or a magnetic resonance imaging (MRI) scan, can indicate a problem with the disc in which the device 500 is implanted. A healthcare provider can manipulate the performance of the device 500 by accessing the remote access component 520.

The device, such as device 500 illustrated in FIG. 5, can be included in a housing. The housing can form a cylinder, sphere, capsule, disc, cone, coil shape, or any combination thereof. In an example, the housing can surround each of the components of the device. Alternatively, the individual components can be included within one or more housings. For example, controller can be included in a housing. The reservoir can be at least partially included within the housing, can extend beyond the boundaries of the housing, or can be separate from the housing. In another example, the sensor can be included in a housing with the controller, and the power supply and the remote access component can be housed separately.

The housing can have a smallest dimension not greater than about 8 mm. For example, the smallest dimension can be not greater than about 5 mm, such as not greater than about 3 mm. In a particular example, a cylindrical housing can have a diameter that is not greater than about 8 mm. In an exemplary capsule-shaped housing, the diameter around the center is not greater than about 8 mm.

The housing can be formed of a metallic material, a polymeric material, or any combination thereof. An exemplary polymeric material can include polypropylene, polyethylene, halogenated polyolefin, fluoropolyolefin, polybutadiene, polysulfone, polyaryletherketone, polyuerethane, polyester, or copolymers thereof, silicone, polyimide, polyamide, polyetherimide, a hydrogel, or any combination thereof. An exemplary polyaryletherketone (PAEK) material can include polyetherketone (PEK), polyetheretherketone (PEEK), polyetherketoneketone (PEKK), polyetherketoneetherketoneketone (PEKEKK), or any combination thereof. An exemplary silicone can include dialkyl silicones, fluorosilicones, or any combination thereof. An exemplary hydrogel can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or any combination thereof. An exemplary metallic material includes stainless steel, titanium, platinum, tantalum, gold or their alloys as well as gold-plated ferrous alloys, platinum-plated ferrous alloys, cobalt-chromium alloys or titanium nitride coated stainless steel, or any combination thereof.

Figure 6:
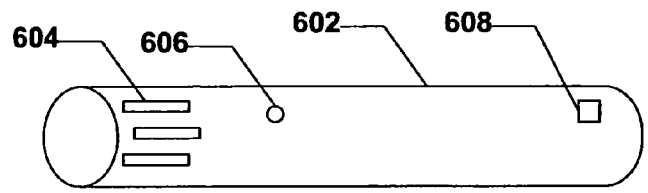
FIG. 6, FIG. 7, FIG. 8, FIG. 9, and FIG. 10 include views of exemplary controlled release devices.

FIG. 6, FIG. 7, FIG. 8, FIG. 9, and FIG. 10 include illustrations of devices surrounded by housings. FIG. 6 includes an example of an exemplary device 602 that includes external ports 604 connected to control elements for providing access to reservoirs. In addition, the exemplary device 602 includes a port 608 coupled to a sensor via which the sensor can acquire data associated with the condition of surrounding tissue, such as the nucleus pulposus. In a further example, the device 602 can include a refill port 606 for refilling a reservoir with an agent.

Figure 7:
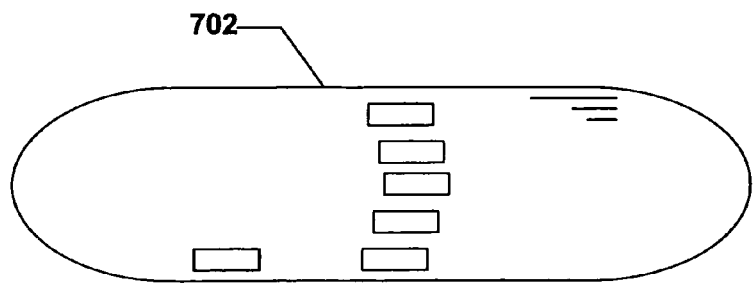
Figure 8:
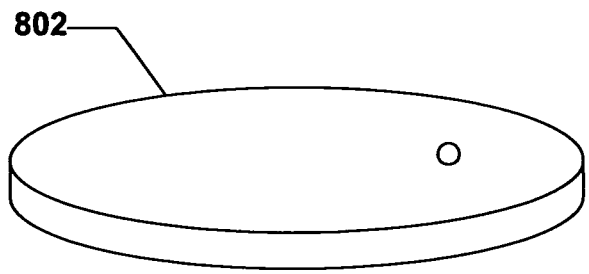

FIG. 7 illustrates another exemplary device 702 in the shape of a capsule and FIG. 8 illustrates a further exemplary device 802 in the shape of a disc. The exemplary devices 702 and 802 can include ports for sensor access, reservoir access, and refill access.

Figure 9:
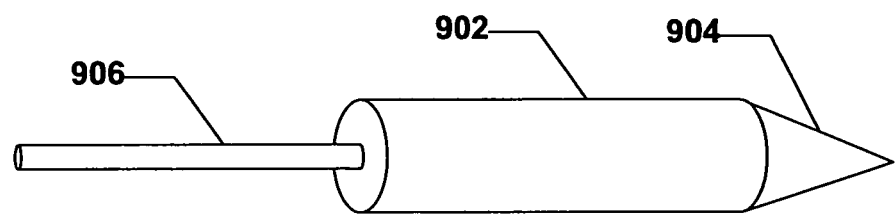

FIG. 9 includes a further exemplary device 902. The device 902 can include a conical end 904 to assist with insertion of the device in the nucleus pulposus. In addition, a reservoir 906 can extend beyond the end of the housing. The device 902 can also include ports for refill, reservoir access, and sensor access. In a particular example, the reservoir 906 can be flexible. As such, the reservoir 906 can coil when inserted in the nucleus pulposus.

Figure 10:
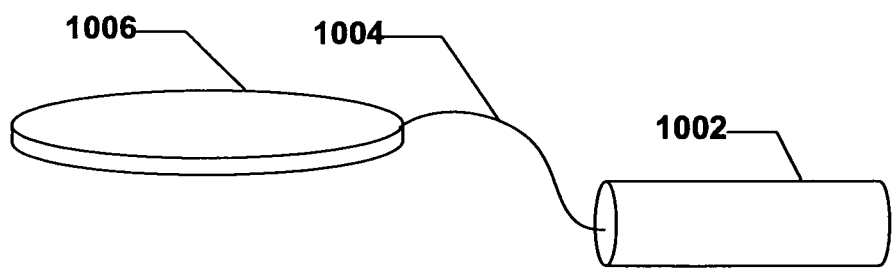

In another exemplary embodiment illustrated in FIG. 10, a device 1000 includes separate housings 1002 and 1006 connected by a transmission line 1004. In an exemplary embodiment, the housing 1002 can include a controller, a sensor, and a control element, and the housing 1006 can include a power supply and a remote access component. In such an example, power is transmitted along line 1004 to the controller in the housing 1002. In a further example, the housing 1002 can include a sensor and a control element and the housing 1006 can include a controller, a memory, and a remote access component. In such an example, sensor signals and control signals are transmitted along transmission line 1004. In a particular example, the transmission line 1004 can include a conduit for an agent and an electrical signal line.

Figure 11:
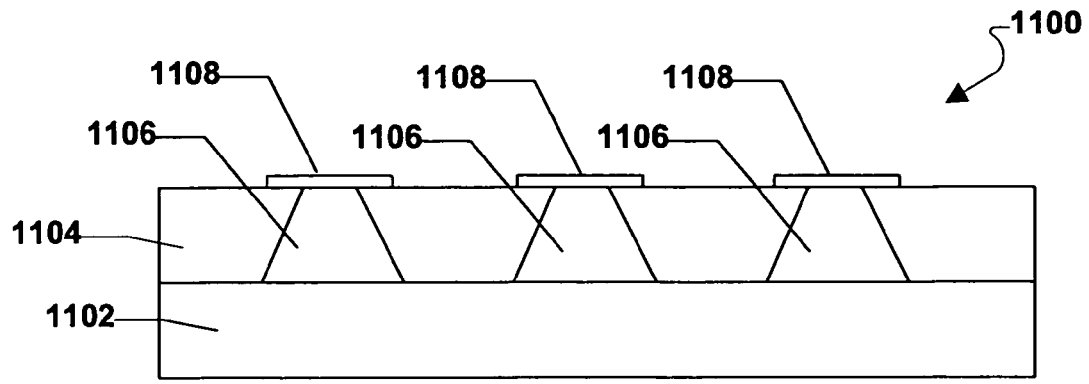
FIG. 11 includes a cross-section of an exemplary reservoir portion of an exemplary controlled release device.

In a further embodiment, the implanted device can include an array of reservoirs. For example, FIG. 11 includes an illustration of an exemplary array of reservoirs. For example, a device can include a substrate 1102. Imposed over the substrate is a layer 1104 forming an array of reservoirs 1106. The array of reservoirs 1106 can each include an agent. Alternatively, a first subset of the array of reservoirs 1106 can include a first agent and a second subset of the array of reservoirs 1106 can include a second agent. Each reservoir 1106 is separated from surrounding tissue by a removable or destructible barrier 1108. In an exemplary embodiment, the barrier 1108 can be burst in response to expansion of a substance included in the reservoir 1106. For example, the substance can expand in response to heat or electrical current. In a further example, heat or an electrical current can be applied to the barrier 1108, causing the barrier to disintegrate and exposing the agent in the reservoir 1106 to surrounding tissue. Exemplary barrier materials include metals such as copper, gold, silver, and zinc, and some polymers. An exemplary polymer has a melting point above body temperature. When the local temperature near the polymer barrier layer is increased above the polymer's melting point by thin film resistors located near the barrier layer, the barrier layer melts and exposes the contents of the reservoir to the surrounding environment.

Exemplary Methods of Use

Figure 12:
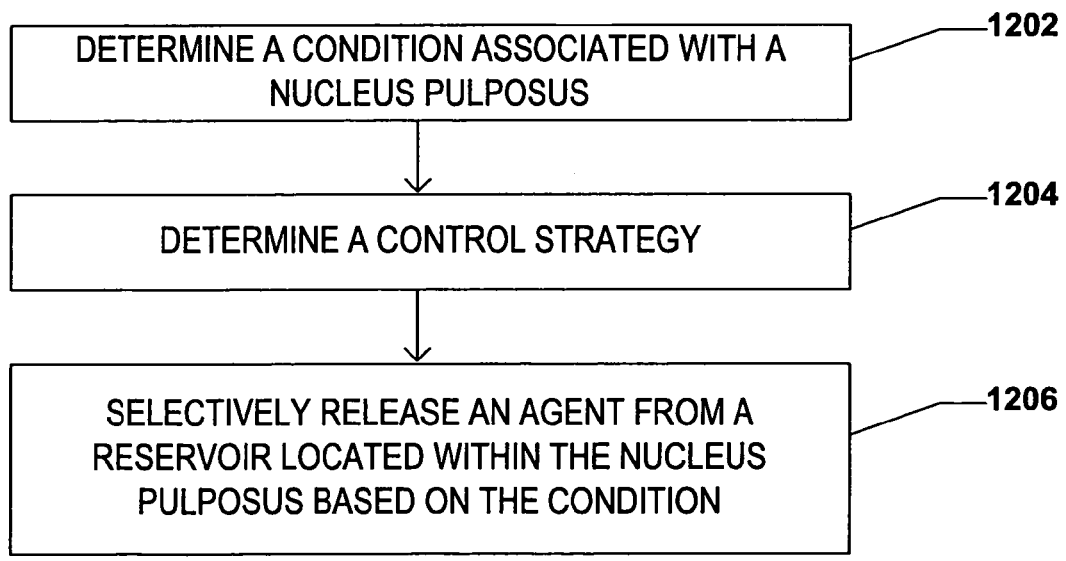
FIG. 12, FIG. 13, and FIG. 14 include block flow diagrams of exemplary methods for use by an exemplary controlled release device.

In an exemplary method, the device includes a controller that measures a condition of a surrounding nucleus pulposus and releases an agent based on the measurement. As illustrated at 1202 of FIG. 12, the device can determine a condition associated with a nucleus pulposus. For example, the device can include a sensor, such as a pressure sensor, moisture sensor, resistivity or conductivity sensor, pH sensor, or any combination thereof. The device can use signals from the one or more sensors to determine a condition of the nucleus pulposus. For example, a high average pressure measurement or a pressure measurement that is too high at a particular time of day can indicate excess hydration. In contrast, a low average pressure measurement can indicate a low hydration. In another example, the moisture sensor can indicate a high or low hydration level. In a further example, a combination of pressure data and moisture data can be used in determining the condition of the nucleus pulposus. In an additional example, a trend in data from one or more sensor or a rate of change of a sensor measurement can be used in determining the condition of the nucleus pulposus.

Figure 19:
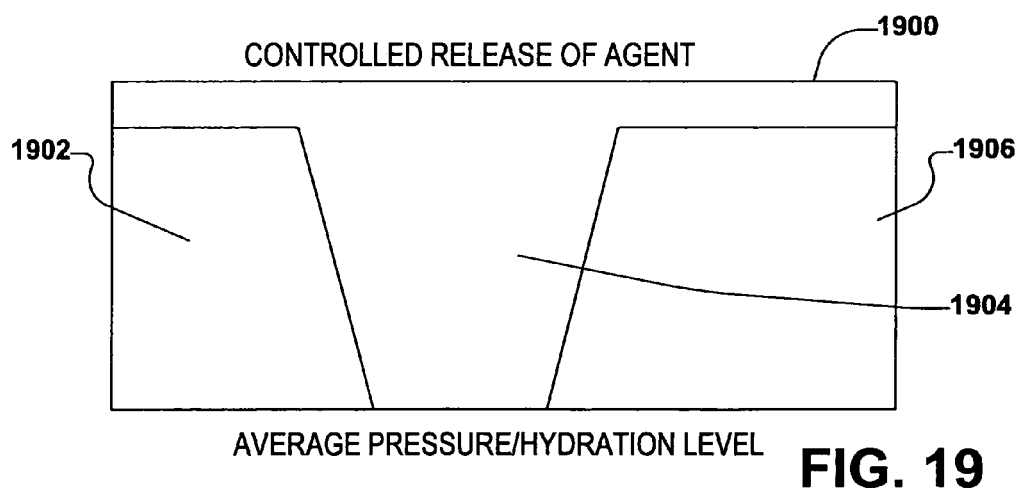
FIG. 19 includes an illustration of an exemplary controlled release strategy.

Based on the condition of the nucleus pulposus, the controller can determine a control strategy, as illustrated at 1204. For example, the controller can select an agent to be dispensed and can determine a dosage to be dispensed. In a particular example illustrated in FIG. 19, the controller can release agents in accordance with the control strategy 1900. For low pressure or hydration levels, a stimulating agent can be released, as illustrated at 1902. For a moderate pressure or hydration level, no agent is released, as illustrated at 1904, and for a high pressure or hydration level, a degrading agent can be released, as illustrated at 1906.

In response to determining the condition of the nucleus pulposus, the controller can initiate the release of an agent. For example, the controller can selectively release an agent from a reservoir that is at least partially located within the nucleus pulposus based on the condition, as illustrated at 1206. In a particular example, the controller can select an agent to release, determine a dosage or amount of agent to release, and manipulated a control element, based on the determined condition of the nucleus pulposus.

Figure 13:
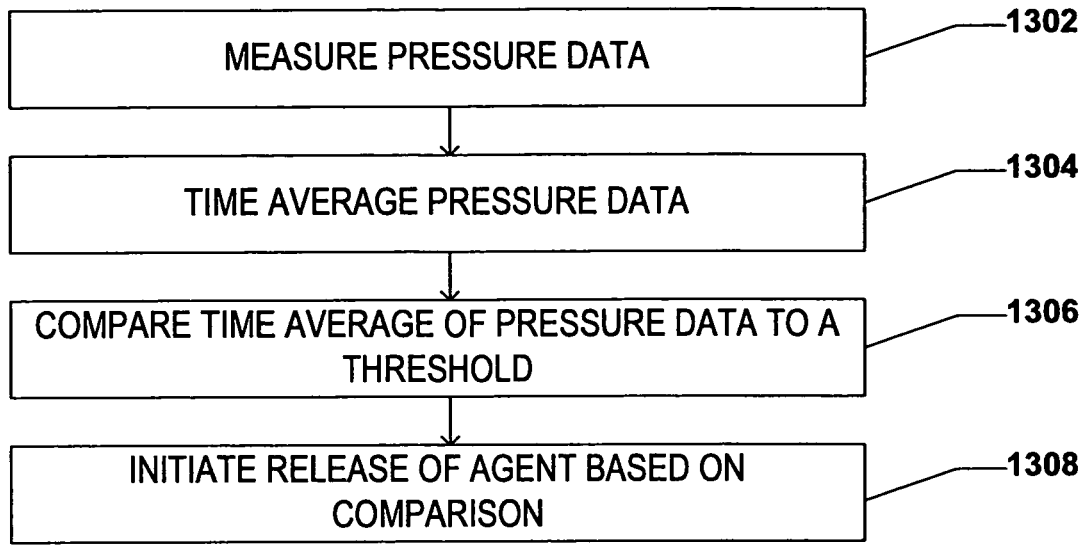
Figure 14:
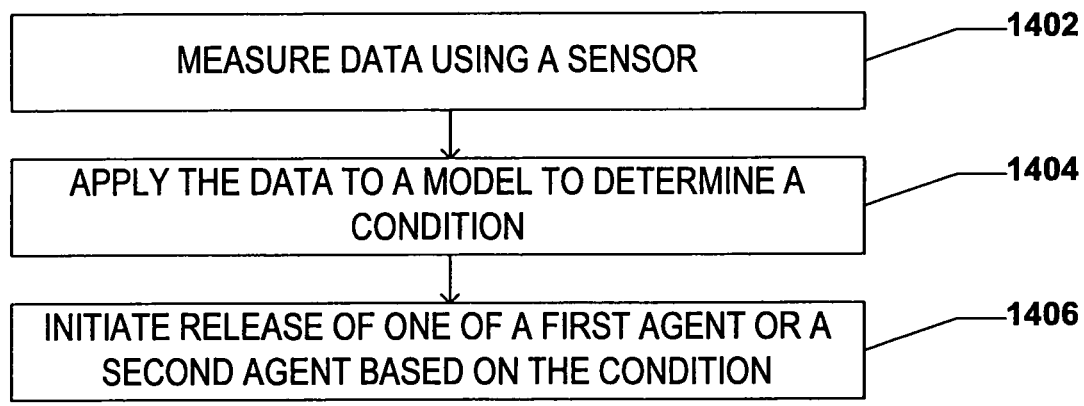

In a particular embodiment, the device can access pressure data, as illustrated at 1302 of FIG. 13. For example, the device can receive pressure data from a sensor or can retrieve pressure data from memory. The device can average the pressure data, such as determine a time average mean of the pressure data, as illustrated at 1304. In another example, the device can average a minimum pressure or a maximum pressure for a set of days. In a further example, the device can average pressure measured at a particular time of day, such as when a patient is inactive.

The device can compare the average of the pressure data to a threshold, as illustrated at 1306. For example, the threshold can be a low level threshold below which a stimulating agent is to be released. In another example, the threshold can be a high level threshold above which a degrading agent is to be released.

Based on the comparison to the threshold, the device can release an agent, as illustrated at 1308. For example, a controller can activate a control element associated with a reservoir including the agent to be released. In another example, the controller can activate a reservoir driver.

In another exemplary embodiment, a model can be used to determine when and how much agent is to be released. For example, data can be measured by one or more sensors, as illustrated at 1402. The data can be applied to a model to determine a condition of the nucleus pulposus or determine dosages and agents to be release in association with the condition of the nucleus pulposus, as illustrated at 1404. An exemplary model can include an algebraic model, a neural network model, a fuzzy logic model, or any combination thereof.

Based on the output of the model, the device can initiate release of a first or a second agent, as illustrated at 1406. For example, when the nucleus pulposus is dehydrated, a stimulating agent can be released. In another example, when pressure within the nucleus pulposus is high, a degrading agent can be released.

Device Implantation

Figure 15:
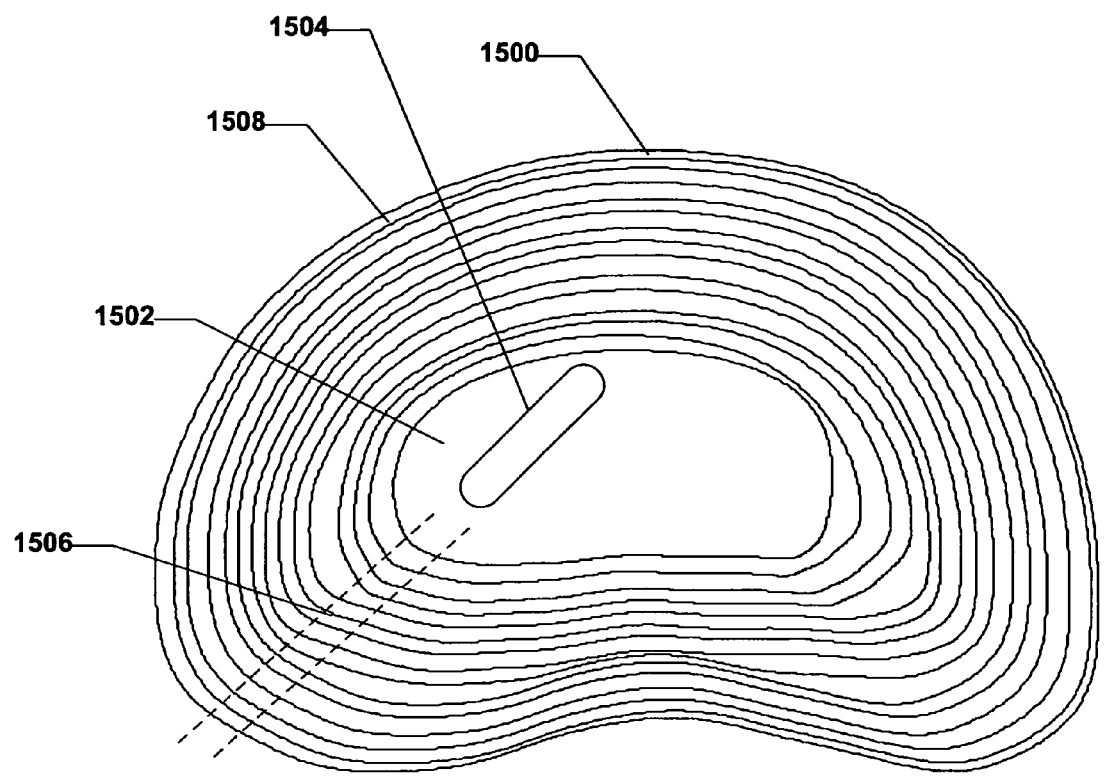
FIG. 15, FIG. 16, and FIG. 17 include illustrations of exemplary controlled release devices in vivo.

The device or at least a portion of the device can be inserted into the nucleus pulposus of an intervertebral disc of a patient. For example, the device can be implanted as a whole within the nucleus pulposus. FIG. 15 includes an illustration of a device 1504 implanted within the nucleus pulposus 1502 of an intervertebral disc 1500. The device 1504 can be inserted through a passage 1506 in the annulus fibrosis 1508 of the intervertebral disc 1500. In an example, the passage 1506 is formed using an instrument having a lumen through which the device 1504 can be guided. Once the device 1504 is inserted into the nucleus pulposus 1502, the passage 1506 in the annulus fibrosis 1508 can be sealed using a tissue sealant, scaffold plug, or any combination thereof. In a particular example, the tissue sealant or scaffold plug includes regenerative agents, such as growth factors.

Figure 16:
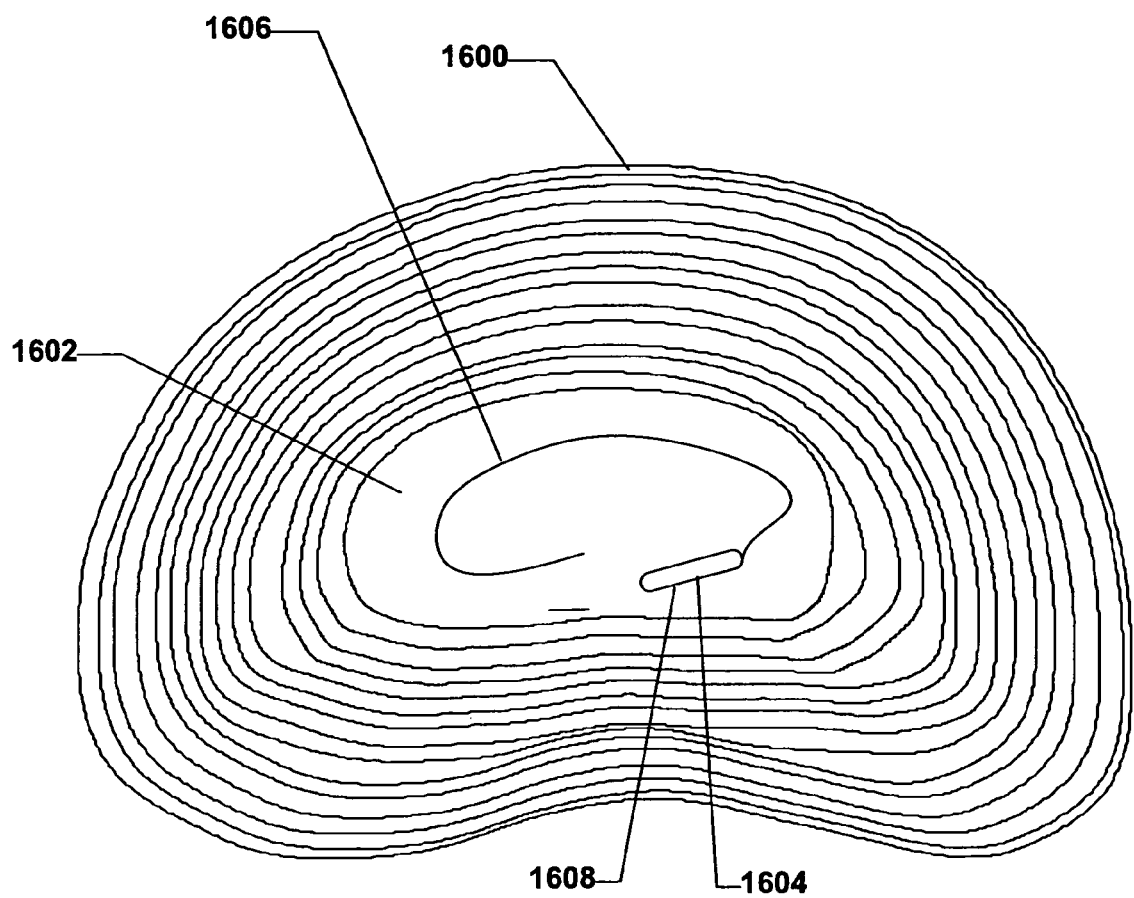

In another exemplary embodiment illustrated in FIG. 16, a device 1604 includes a head 1608 and a flexible tail 1606. The device 1604 can be inserted wholly within the nucleus pulposus 1602 of an intervertebral disc 1600 using the method described above in relation to FIG. 15. The head 1608 can include, for example, a sensor and a controller. The tail 1606 can include a portion of a reservoir. In another example, the tail 1606 can include an antenna.

Figure 17:
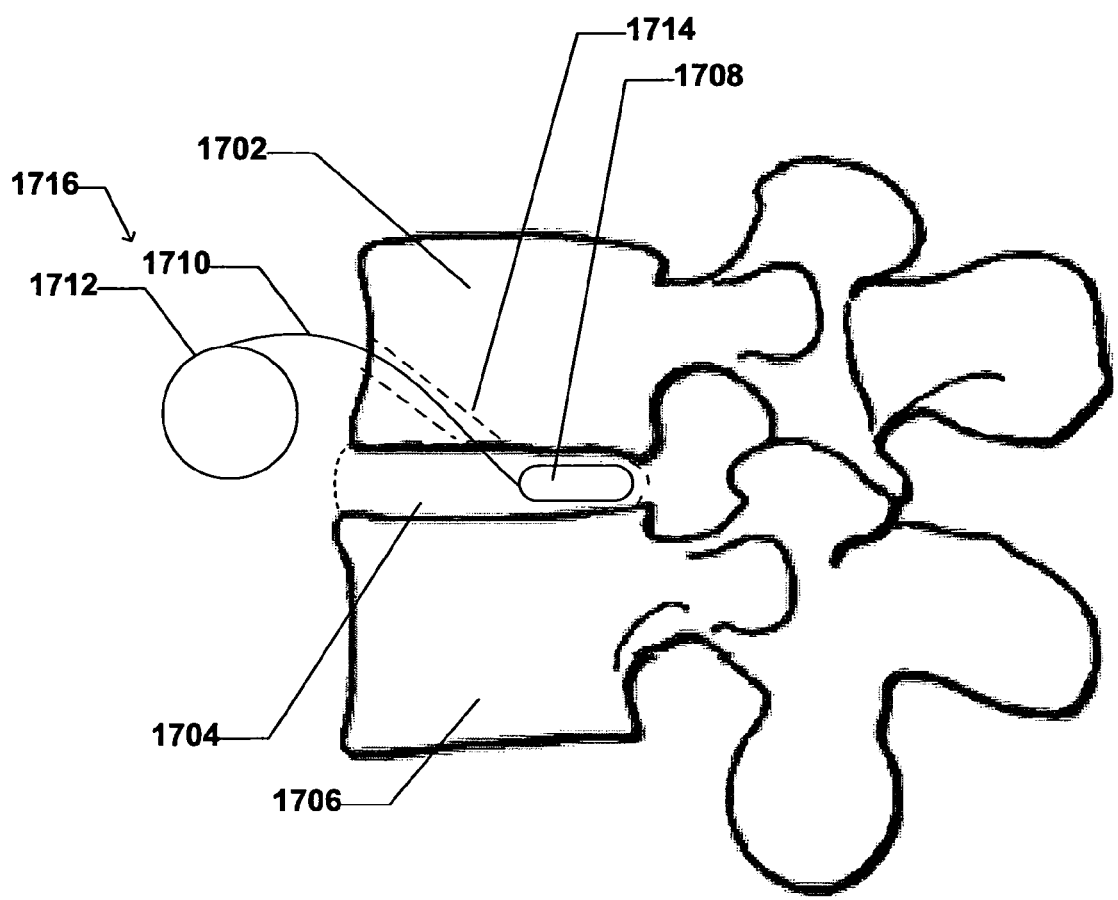

In an alternative embodiment illustrated in FIG. 17, the device can be inserted into the nucleus pulposus of an intervertebral disc 1704 through one of a superior vertebra 1702 or an inferior vertebra 1706. As illustrated in FIG. 17, a portion of the device can be inserted through the vertebral body and the end cap of the superior vertebra 1702. For example, an access 1714 can be drilled through the vertebral body and the end cap of the superior vertebra 1702. A head 1708 of the device 1716 can be guided through the access 1714 into a nucleus pulposus of the intervertebral disc 1704. A transmission line 1710 traverses the access 1714 and connects the head 1708 to a tail 1712 of the device 1716. The access 1714 can be sealed with a ceramic material, bone cement, tissue sealant, or any combination thereof.

In an exemplary embodiment, the head 1708 can include a sensor, a controller, and a control element, and the tail 1712 can include a power supply, a remote access component, and a reservoir refill port. The reservoir can be located at the head 1708 or partially in the tail 1712.

In an alternative example, the head 1708 can include a sensor and a control element. The tail 1712 can include a controller, a memory, a power supply, a remote access component, and at least a portion of a reservoir. As such, the controller can receive data from the sensor and activate the control element from the tail 1712. While two embodiments of the device 1716 are disclosed above, other embodiments can be envisaged.

Patient Treatment using an Implantable Device

Typically, the embodiments of the implantable controlled release device described above can be used to treat conditions associated with an intervertebral disc. For example, a patient can have undergone a prior discectomy or can have experienced a herniated disc. In another example, a scan of the patient, such as a computed tomography (CT) scan or a magnetic resonance imaging (MRI) scan, can indicate a problem in a particular intervertebral disc. In such a case, a device can be implanted in the patient.

In general, the device can be preprogrammed and filed with an agent prior to implantation. For example, the device can include an access port to transfer data, such as dosage data and control data into the device. In another example, the device can include a wireless access circuitry, such as a radiofrequency circuitry, an infrared circuitry, or an ultrasonic circuitry for receiving data. In an example, the wireless access circuitry can be proprietary or can conform to a wireless communication standard, such as IEEE 802.11, IEEE 802.15, or IEEE 802.16. In a particular example, the wireless access circuitry is Bluetooth® compatible. Such data can be determined by a physician or healthcare practitioner prior to inserting the device. Software can be provided to configure the device for a particular patient.

The device can be included in a kit that includes agents to be inserted into the device. Alternatively, the device can be provided with the agent within the device. In addition, the device can include a refill port. An agent can be injected into the port to refill a reservoir.

Figure 18:
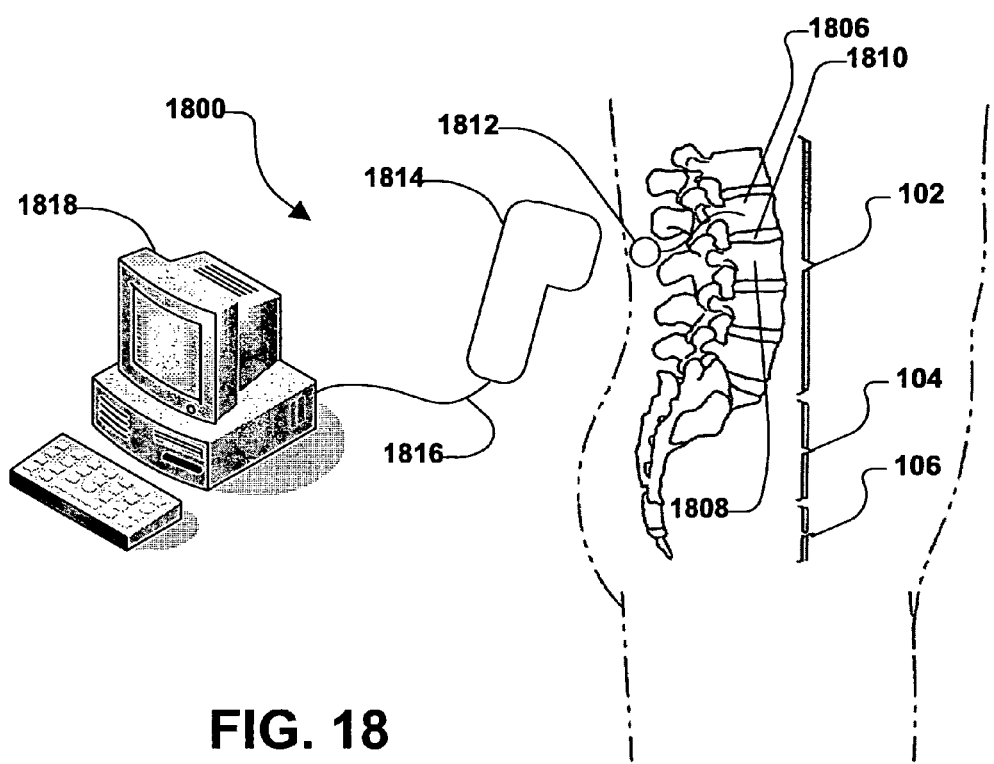
FIG. 18 includes an illustration of an exemplary controlled release system.

In a particular embodiment, the device can provide feedback to a physician or healthcare practitioner when implanted. In the example illustrated at FIG. 18, a device 1812 can be implanted in the spine 1804 of a patient 1802. For example, the device 1812 can include a portion that is inserted in an intervertebral disc 1810 between two vertebrae 1806 and 1808.

The device 1812 can include a wireless access circuitry or a remote access component. A remote access device 1814 located external to the patient 1802 can communicate with the remote access component of the device 1812. For example, the remote access device 1814 can read data from the device 1812. In another example, the remote access device 1814 can transmit parameters or programming instructions to the device 1812.

In a particular embodiment, the remote access device 1814 can be connected to a computer 1818 via a connection 1816. As illustrated, the connection 1816 is a wired connection. Alternatively, the connection 1816 can be wireless.

In an alternative embodiment, the remote access device 1814 can be located at a patient's home. A patient can use the remote access device 1814 to collect data from the implanted device 1812 and forward the data to a physician via the Internet. In addition, the patient can enter additional information via the remote access device 1814 or a computer, such as observations and information about painful events. In a particular example, the remote device can connect over a wired or wireless Internet connection to transmit data to a healthcare practitioner and to receive instructions and parameters from the healthcare practitioner. The remote device 1814 can connect directly. Alternatively, the remote device 1814 can connect to a computer connected to the Internet. In either case, the remote device 1814 can access software, either embedded or at a connected computer, to permit entry of comments by the patient in addition to data received from the implanted device 1812. Furthermore, the computer connected to the device 1814 or the device 1814 itself can provide instructions to the patient. In such a manner, a remotely located healthcare practitioner can remotely monitor performance of the device, the condition of the patient, and manipulate performance of the device.

In an particular example, data retrieved from the implanted device 1812 via the remote device 1814 can be correlated with pain or sensations experienced by the patient. Such a correlation can further enhance the understanding of the healthcare provider, potentially enhancing the treatment of the patient.

CONCLUSION

With the implanted device described above, the condition of an intervertebral disc can be maintained within a range of acceptable states. As such, the chance of herniation, exacerbation of previous herniated injuries, and degradation of the disc can be reduced. Such a device can further reduce the likelihood that a more invasive disc replacement implant is used.

In a particular embodiment, the device also can provide feedback to a healthcare practitioner regarding the state of the intervertebral disc. A healthcare provider can manipulate the performance of the device to provide long term treatment to the intervertebral disc, reducing patient discomfort, patient pain or neuro-deficit, and disc degeneration and delaying additional spinal surgery.

The above-disclosed subject matter is to be considered illustrative, and not restrictive, and the appended claims are intended to cover all such modifications, enhancements, and other embodiments that fall within the true scope of the present invention. For example, it is noted that the components in the exemplary embodiments described herein as having a particular function or as being located in a particular housing are illustrative and it is noted that such components can perform additional functions or be located in different configurations. Thus, to the maximum extent allowed by law, the scope of the present invention is to be determined by the broadest permissible interpretation of the following claims and their equivalents, and shall not be restricted or limited by the foregoing detailed description.

What is claimed is:

1. A device comprising:
a sensor configured to determine a condition associated with a nucleus pulposus;
a reservoir configured to include a first agent capable of affecting the condition associated with the nucleus pulposus;
a control element configured to provide access to the reservoir;
a reservoir driver to motivate the agent to exit the reservoir;
a controller in communication with the sensor, the control element, and the reservoir driver;
the controller configured to manipulate the control element to provide access to the reservoir and manipulate the reservoir driver in response to the condition determined by the sensor; and
a housing containing the sensor, reservoir, control element, reservoir driver and controller, such that the device is adapted to be implanted as a whole into the nucleus pulposus, wherein the housing has at least one dimension of less than 8 mm.

2. The device of claim 1, further comprising a second reservoir configured to include a second agent capable of affecting the condition associated with the nucleus pulposus.

3. The device of claim 2, wherein the first agent includes a stimulating agent and wherein the second agent includes a degrading agent.

4. The device of claim 1, wherein the first agent is a stimulating agent.

5. The device of claim 1, wherein the first agent includes a degrading agent.

6. The device of claim 5, wherein the degrading agent includes a nucleolytic agent.

7. The device of claim 6, wherein the nucleolytic agent includes chymopapain.

8. The device of claim 6, wherein the nucleolytic agent includes chondroitinase ABC.

9. The device of claim 1, wherein the control element includes a valve.

10. The device of claim 1, wherein the condition includes pressure.

11. The device of claim 1, wherein the condition includes hydration level.

12. The device of claim 1, further comprising a housing overlying the controller.

13. The device of claim 1, further comprising a remote access component in communication with the controller.

14. A device comprising:
a sensor configured to determine a condition associated with a nucleus pulposus;
a first reservoir configured to include a stimulating agent;
a second reservoir configured to include a degrading agent;
a first control element configured to provide access to the first reservoir;
a second control element configured to provide access to the second reservoir;
a first reservoir driver to motivate the stimulating agent to exit the reservoir;
a second reservoir driver to motivate the degrading agent to exit the reservoir;
a controller in communication with the sensor, the first reservoir driver, and the second reservoir driver, the controller configured to manipulate the first control element and the second control element to selectively initiate access to the first reservoir or the second reservoir and manipulate the first reservoir driver or second reservoir driver in response to the condition determined by the sensor; and
a housing containing the sensor, first reservoir, second reservoir, first control element, second control element, first reservoir driver, second reservoir driver and controller, such that the device is adapted to be implanted as a whole into the nucleus pulposus, wherein the housing has at least one dimension of less than 8 mm.

15. The device of claim 14, further comprising a control element configured to provide access to the first reservoir.

16. The device of claim 14, wherein the degrading agent includes a nucleolytic agent.

17. The device of claim 16, wherein the nucleolytic agent includes chymopapain.

18. The device of claim 14, further comprising a remote access component in communication with the controller.

19. A device comprising:
a sensor configured to determine a condition associated with a nucleus pulposus;
a first reservoir configured to include a first agent;
a first reservoir driver coupled to the first reservoir and configured to effect the release of the first agent from the first reservoir;
a control element configured to provide access to the reservoir;
a controller in communication with the sensor;
a remote access component in communication with the controller, wherein the controller is configured to manipulate the control element to provide access to the reservoir and configured to manipulate the first reservoir driver to effect the release of the first agent in response to the condition received from the sensor and a first signal received via the remote access component; and
a housing containing the sensor, first reservoir, control element, first reservoir driver, and controller, such that the device is adapted to be implanted as a whole into the nucleus pulposus, wherein the housing has at least one dimension of less than 8 mm.

20. The device of claim 19, wherein the controller is configured to manipulate the first reservoir driver to prevent release of the first agent in response to a second signal received via the remote access component.

21. The device of claim 19, further comprising a second reservoir configured to include a second agent.

* * * * *